(12) United States Patent
Altman et al.

(10) Patent No.: US 8,415,346 B2
(45) Date of Patent: Apr. 9, 2013

(54) INHIBITORS OF JANUS KINASES

(75) Inventors: Michael Altman, Needham, MA (US);
Kevin Wilson, West Newton, MA (US)

(73) Assignee: Merck Sharp & Dohme Corp.,
Rahway, NJ (US)

( * ) Notice: Subject to any disclaimer, the term of this patent is extended or adjusted under 35 U.S.C. 154(b) by 0 days.

(21) Appl. No.: 13/056,180

(22) PCT Filed: Jul. 21, 2009

(86) PCT No.: PCT/US2009/051192
§ 371 (c)(1),
(2), (4) Date: Jan. 27, 2011

(87) PCT Pub. No.: WO2010/014453
PCT Pub. Date: Feb. 4, 2010

(65) Prior Publication Data
US 2011/0130393 A1 Jun. 2, 2011

Related U.S. Application Data

(60) Provisional application No. 61/137,475, filed on Jul. 31, 2008.

(51) Int. Cl.
*A61K 31/541* (2006.01)
*A61K 31/5377* (2006.01)
*A61K 31/496* (2006.01)
*C07D 231/38* (2006.01)
*C07D 413/12* (2006.01)
*C07D 403/12* (2006.01)
*C07D 417/12* (2006.01)

(52) U.S. Cl. ............ 514/227.8; 514/236.5; 514/254.05; 514/407; 544/58.2; 544/140; 544/371; 548/371.7

(58) Field of Classification Search ................... None
See application file for complete search history.

(56) References Cited

U.S. PATENT DOCUMENTS
7,179,836 B2    2/2007   Adams et al.

FOREIGN PATENT DOCUMENTS
WO    2006119542 A1    11/2006
WO    2008052974 A1    5/2008

*Primary Examiner* — Kamal Saeed
(74) *Attorney, Agent, or Firm* — Laura M. Ginkel; David A. Muthard

(57) ABSTRACT

The instant invention provides for compounds that inhibit the four known mammalian JAK kinases (JAK1, JAK2, JAK3 and TYK2). The invention also provides for compositions comprising such inhibitory compounds and methods of inhibiting the activity of JAK1, JAK2, JAK3 and TYK2 by administering the compound to a patient in need of treatment for myeloproliferative disorders or cancer.

8 Claims, No Drawings

INHIBITORS OF JANUS KINASES

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145 (Gao FEES Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) as reported that STAT3 is constitutively activated v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3−/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

SUMMARY OF THE INVENTION

The instant invention provides for compounds that inhibit mammalian JAK kinases (such as JAK1, JAK2, JAK3 and TYK2). The invention also provides for compositions comprising such inhibitory compounds and methods of inhibiting the activity of JAK1, JAK2, JAK3 and TYK2 by administering the compound to a patient in need of treatment for myeloproliferative disorders or cancer. One embodiment of the invention is illustrated by a compound of formula I, and the pharmaceutically acceptable salts and stereoisomers thereof:

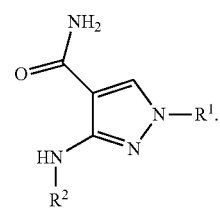

DETAILED DESCRIPTION OF THE INVENTION

The instant invention provides for compounds that inhibit the four known mammalian JAK kinases (JAK1, JAK2, JAK3 and TYK2). The invention also provides for compositions comprising such inhibitory compounds and methods of inhibiting the activity of JAK1, JAK2, JAK3 and TYK2 by administering the compound to a patient in need of treatment for myeloproliferative disorders or cancer. One embodiment of the invention is illustrated by a compound of formula I:

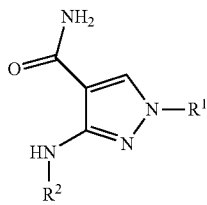

wherein $R^1$ is aryl, which is optionally substituted with one to three substituents independently selected from the group consisting of halo, hydroxyl, cyano, $SO_2R^3$, $C_{1-6}$ alkyl and heterocyclyl; wherein said alkyl group is optionally substituted with one to three halo, hydroxyl or cyano, and said heterocyclyl group is optionally substituted on either the carbon or heteroatom with one to three halo, hydroxyl or oxo;

$R^2$ is aryl or heteroaryl, wherein said aryl and heteroaryl groups are optionally substituted on either the carbon or heteroatom with one to three substituents selected from the group consisting of halo, cyano, $C_{1-6}$ alkyl, heterocyclyl, (C=O)heterocyclyl, (C=O)$R^3$, (C=O)O$R^3$, (C=O)$NR^3R^4$, $SO_2R^3$, $SO_2NR^3R^4$, $NR^3SO_2R^4$ and $SO_2$(heterocyclyl); wherein said alkyl group is optionally substituted with one to three halo, hydroxyl, O(C=O)$NR^3R^4$, heteroaryl, heterocyclyl or $NR^3R^4$; said heterocyclyl groups are optionally substituted on either the carbon or heteroatom with one to two groups independently selected from the group consisting of $C_{1-3}$ alkyl, hydroxyl and oxo; and said heteroaryl groups are optionally substituted on either the carbon or heteroatom with $C_{1-3}$ alkyl;

$R^3$ is hydrogen or $C_{1-6}$ alkyl;
$R^4$ is hydrogen or $C_{1-6}$ alkyl;
or a pharmaceutically acceptable salt thereof.

In an embodiment of the invention, $R^1$ is aryl, wherein said aryl group is substituted with one to three substituents independently selected from the group consisting of halo and $C_{1-6}$ alkyl, wherein said alkyl group is optionally substituted with hydroxyl. In a class of the invention, $R^1$ is phenyl, wherein said phenyl group is substituted with one to three halo.

In an embodiment of the invention, $R^2$ is aryl or heteroaryl, wherein said aryl and heteroaryl groups are optionally substituted on either the carbon or heteroatom with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl, heterocyclyl or $NR^3R^4$; said heterocyclyl groups are optionally substituted on either the carbon or heteroatom with one to two groups independently selected from the group consisting of $C_{1-3}$ alkyl and oxo. In a class of the invention, $R^2$ is aryl, wherein said aryl group is optionally substituted with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl, heterocyclyl or $NR^3R^4$; said heterocyclyl groups are optionally substituted on either the carbon or heteroatom with one to two groups independently selected from the group consisting of $C_{1-3}$ alkyl and oxo. In a subclass of the invention, $R^2$ is phenyl, wherein said phenyl group is optionally substituted with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl or heterocyclyl; said heterocyclyl groups are optionally substituted on either the carbon or heteroatom with one to two groups independently selected from the group consisting of $C_{1-3}$ alkyl, and oxo.

Reference to the preferred embodiments set forth above is meant to include all combinations of particular and preferred groups unless stated otherwise.

Specific embodiments of the present invention include, but are not limited to:
3-{[4-(methylsulfonyl)phenyl]amino}-1-phenyl-1H-pyrazole-4-carboxamide;
3-({4-[(methylamino)carbonyl]phenyl}amino)-1-phenyl-1H-pyrazole-4-carboxamide;
3-{[2-(hydroxymethyl)pyridin-4-yl]amino}-1-phenyl-1H-pyrazole-4-carboxamide;
3-{[4-(morpholin-4-ylcarbonyl)phenyl]amino}-1-phenyl-1H-pyrazole-4-carboxamide;
3-{[4-(morpholin-4-ylsulfonyl)phenyl]amino}-1-phenyl-1H-pyrazole-4-carboxamide;
3-({4-[(dimethylamino)sulfonyl]phenyl}amino)-1-phenyl-1H-pyrazole-4-carboxamide;
3-({4-[(dimethylamino)carbonyl]phenyl}amino)-1-phenyl-1H-pyrazole-4-carboxamide;
3-anilino-1-phenyl-1H-pyrazole-4-carboxamide;
3-({4-[(4-methylpiperazin-1-yl)carbonyl]phenyl}amino)-1-phenyl-1H-pyrazole-4-carboxamide;
3-({4-[(1,1-dioxidothiomorpholin-4-yl)carbonyl]phenyl}amino)-1-phenyl-1H-pyrazole-4-carboxamide;
3-{[4-(morpholin-4-ylmethyl)phenyl]amino}-1-phenyl-1H-pyrazole-4-carboxamide;
3-({4-[(1,1-dioxidothiomorpholin-4-yl)methyl]phenyl}amino)-1-phenyl-1H-pyrazole-4-carboxamide;
3-({4-[(dimethylamino)methyl]phenyl}amino)-1-phenyl-1H-pyrazole-4-carboxamide;
3-{[4-(1-hydroxy-1-methylethyl)phenyl]amino}-1-phenyl-1H-pyrazole-4-carboxamide;
1-(4-chlorophenyl)-3-{[4-(methylsulfonyl)phenyl]amino}-1H-pyrazole-4-carboxamide;
1-[4-(methylsulfonyl)phenyl]-3-{[4-(methylsulfonyl)phenyl]amino}-1H-pyrazole-4-carboxamide;
1-(4-tert-butylphenyl)-3-{[4-(methylsulfonyl)phenyl]amino}-1H-pyrazole-4-carboxamide;
1-[4-(1-hydroxyethyl)phenyl]-3-{[4-(methylsulfonyl)phenyl]amino}-1H-pyrazole-4-carboxamide;
or a pharmaceutically acceptable salt thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

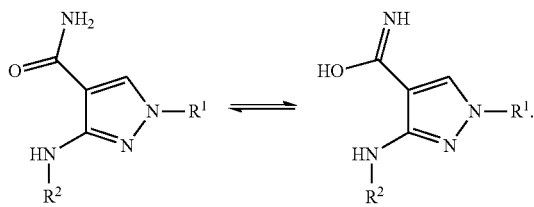

Many heteroaryl groups, such as imidazoles, exist as a mixture of 1H/2H tautomers. The tautomeric forms of these heteroaryl moieties are also within the scope of the instant invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_{1-6}$, as in "$(C_{1-6})$alkyl" is defined to include groups having 1, 2, 3, 4, 5, or 6 carbons in a linear or branched arrange-ment. For example, "$(C_{1-6})$alkyl" specifically includes methyl, ethyl, n-propyl, i-propyl, n-butyl, t-butyl, i-butyl, pentyl, hexyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaaryl moieties include but are not limited to: 2-benzimidazolyl, 2-quinolinyl, 3-quinolinyl, 4-quinolinyl, 1-isoquinolinyl, 3-isoquinolinyl, 4-isoquinolinyl, dihydroimidazopyrazinyl and dihydrooxozolopyridinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. Further examples of "heterocyclyl" include, but are not limited to the following: azabicyclohexyl, azaphosphinyl, azaspiroheptyl, benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, dioxidothiomorpholinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, oxadiazaspirodecyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK1, JAK2, JAK 3, and TYK2, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther*. (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydro gels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin, MLN-341 (Velcade) and carfilzomib.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]aeridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M.Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. Nos. 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Burne-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-6 are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.*, 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93106099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileuldn diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyte®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor; a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The abbreviations used herein have the following tabulated meanings. Abbreviations not tabulated below have their meanings as commonly used unless specifically stated otherwise.

| | |
|---|---|
| Ac | acetyl |
| Bn | benzyl |
| $CHCl_3$ | chloroform |
| $Cu(OAc)_2$ | copper acetate |
| DCM | dichloromethane |
| DIPEA | diisopropylethylamine |
| DMF | N,N-dimethylformamide |
| DMSO | dimethyl sulfoxide |
| EDC | 1-ethyl-3-(3-dimethylaminopropyl) carbodiimide hydrochloride |
| EtOAc | ethyl acetate |
| EtOH | ethanol |
| HCl | hydrogen chloride |
| $H_2O_2$ | hydrogen peroxide |
| $H_2SO_4$ | hydrogen sulfide |
| $K_2CO_3$ | potassium carbonate |
| MeOH | methanol |
| $MgSO_4$ | magnesium sulfide |
| Ms | methanesulfonyl = mesyl = $SO_2Me$ |
| $NH_4Cl$ | ammonium chloride |
| NaOH | hydrazine |

| | |
|---|---|
| NaHCO₃ | N-methylmorpholine-N-oxide |
| NSAID | non-steroidal anti-inflammatory drug |
| Pd₂dba₃ | tris(dibenzylideneacetone)dipalladium(0) |
| Pd(PPh₃)₄ | tetrakis(triphenylphosphine)palladium (I) |
| Ph | phenyl |
| PhB(OH)₂ | phenyl boronic acid |
| POCl₃ | phorphorous oxychloride |
| r.t. | room temperature |
| Rac. | racemic |
| SEM | 2-(trimethylsilyl)ethoxymethoxy |
| TEA | triethylamine |
| TFA | trifluoroacetic acid |
| THF | tetrahydrofuran |
| TLC | thin layer chromatography |

Alkyl Group Abbreviations

| | |
|---|---|
| Me | Methyl |
| Et | Ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

The compounds of the present invention can be prepared according to the following general schemes, using appropriate materials, and are further exemplified by the subsequent specific examples. The compounds illustrated in the examples are not, however, to be construed as forming the only genus that is considered as the invention. The illustrative Examples below, therefore, are not limited by the compounds listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

Methods of Synthesis

Method 1

General procedures to prepare compounds of the instant invention are described in Scheme 1. Hydrazide I can be condensed with (ethoxymethylene)malononitrile to yield pyrazole enamine II. The enamine can be hydrolyzed under acidic conditions to provide 3-amino pyrazoles III and IV. Cyano pyrazole III can be subsequently hydrated to provide amido pyrazole IV. The 3-amino pyrazole IV can be elaborated to the final product pyrazole V through a palladium catalyzed coupling with an appropriate optionally substituted halogenated (hetero)aromatic.

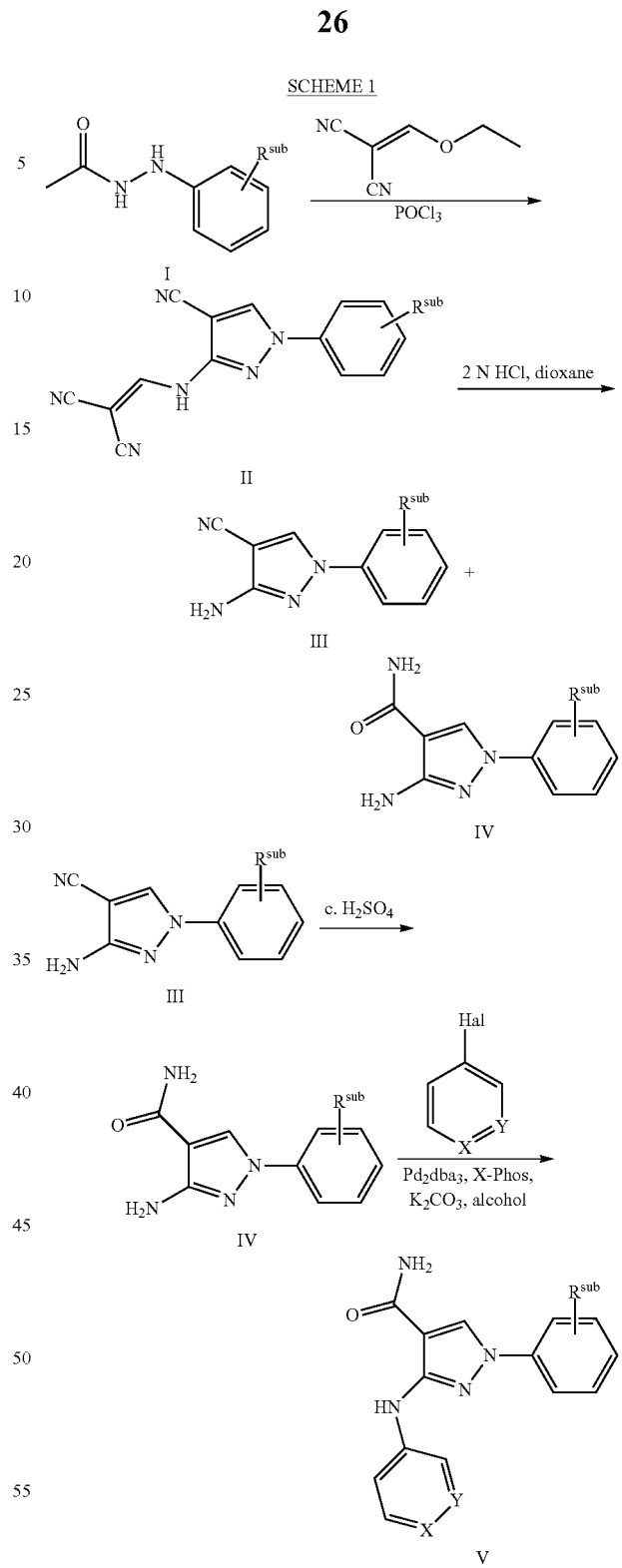

SCHEME 1

Method 2

General procedures to prepare compounds of the instant invention are described in Scheme 2. 3-amino-1H-pyrazole-4-carbonitrile VI can be arylated with phenylboronic acid to yield a mixture of anilino pyrazole VII-A and 3-amino pyrazole III. The 3-amino pyrazole III can be elaborated to pyrazole VII through a palladium catalyzed coupling with an appropriate optionally substituted halogenated (hetero)aromatic. The final product pyrazole V can be obtained by hydration of cyano pyrazole VII.

removed by acid hydrolysis to yield pyrazole X. The 3-arylamino pyrazole X can be elaborated to pyrazole VII through a copper catalyzed arylation with an appropriate optionally substituted arylboronic acid. The final product pyrazole V can be obtained by hydration of cyano pyrazole VII.

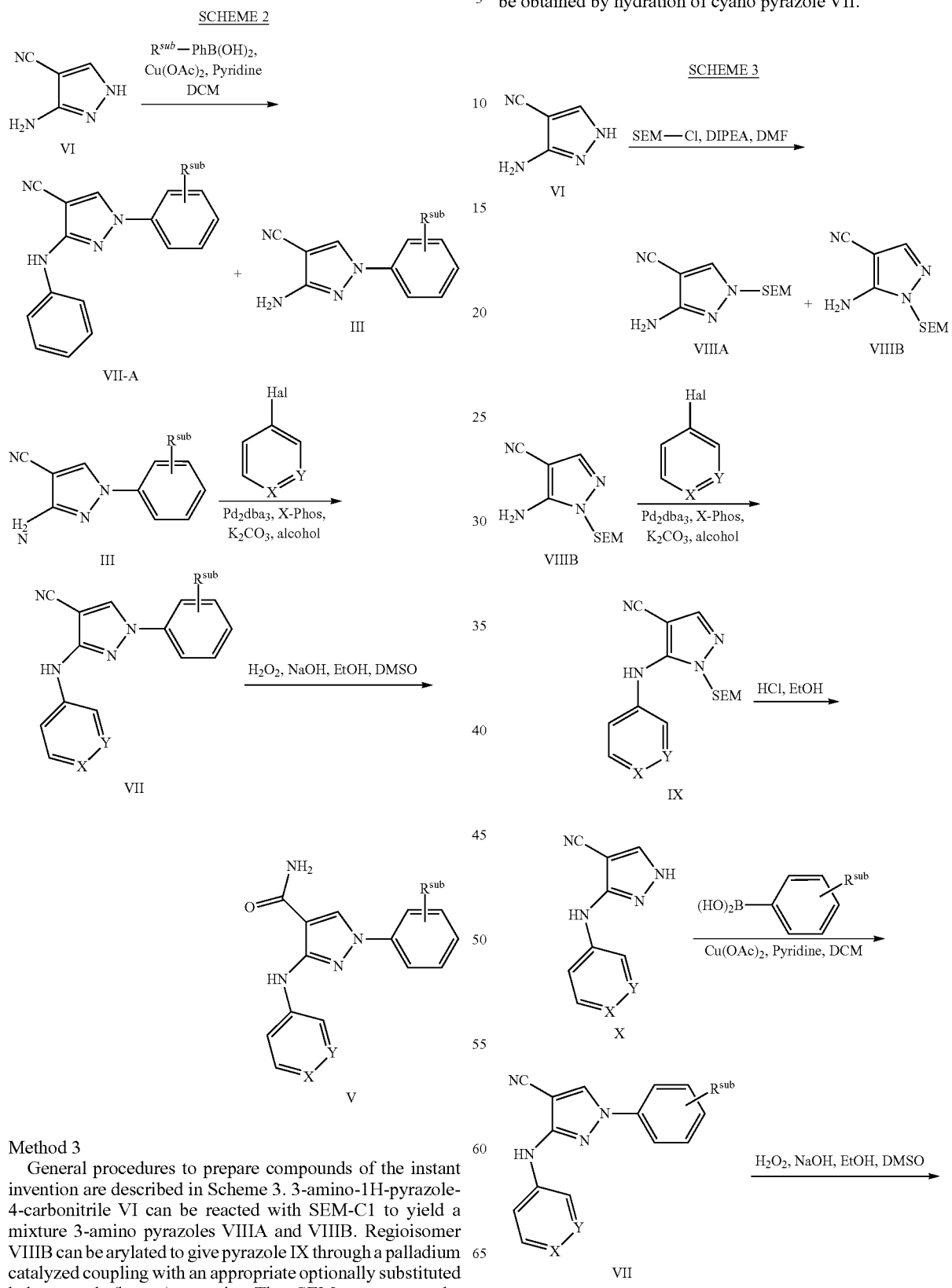

Method 3

General procedures to prepare compounds of the instant invention are described in Scheme 3. 3-amino-1H-pyrazole-4-carbonitrile VI can be reacted with SEM-Cl to yield a mixture 3-amino pyrazoles VIIIA and VIIIB. Regioisomer VIIIB can be arylated to give pyrazole IX through a palladium catalyzed coupling with an appropriate optionally substituted halogenated (hetero)aromatic. The SEM group can be -continued

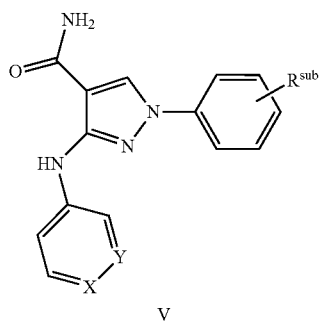

V

The invention will now be illustrated in the following non-limiting examples in which, unless otherwise stated:
1. All final products were analyzed by NMR, LCMS.
2. Intermediates were analyzed by NMR and/or TLC and/or LCMS.
3. Most compounds were purified by flash chromatography on silica gel, reverse phase HPLC, recrystallization, and/or swish (suspension in a solvent followed by filtration of the solid).
4. The course of the reactions was followed by thin layer chromatography (TLC) and/or LCMS and reaction times are given for illustration only.

EXAMPLE 1

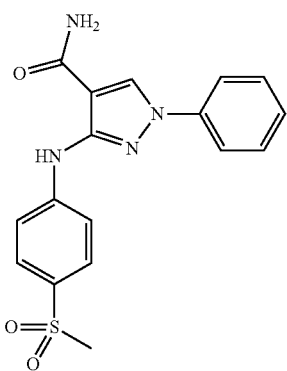 [SMILES: CS(=O)(=O)c1ccc(Nc2nn(-c3ccccc3)cc2C(N)=O)cc1]

3-{[4-(methylsulfonyl)phenyl]amino}-1-phenyl-1H-pyrazole-4-carboxamide

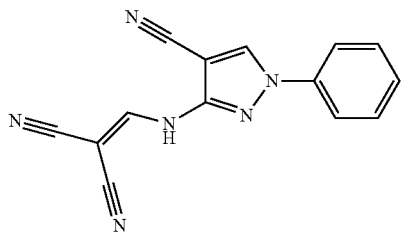 [SMILES: N#CC(C#N)=CNc1nn(-c2ccccc2)cc1C#N]

Step 1. {[(4-cyano-1-phenyl-1H-pyrazol-3-yl)amino]methylene}malononitrile

N'-phenylacetohydrazide (5 g, 33.3 mmol) and (ethoxymethylene)malononitrile (8.13 g, 66.6 mmol) were stirred in phosphorus oxychloride (6.21 ml, 66.6 mmol) at 100° C. for 30 minutes. Room temperature was attained, water was added and the dark solid collected by filtration. The residue was triturated in EtOH to give {[(4-cyano-1-phenyl-1H-pyrazol-3-yl)amino]methylene}malononitrile as a beige solid (batch 1). The filtrate was concentrated in vacuo and the residue purified by MPLC (6-50% EtOAc-hexanes) to give {[(4-cyano-1-phenyl-1H-pyrazol-3-yl)amino]methylene}malononitrile as an orange solid after recrystallizing from EtOAc-hexanes (batch 2).

LRMS (APCI) calc'd for ($C_{14}H_9N_6$) [M+H]$^+$: 261, Found: 261.

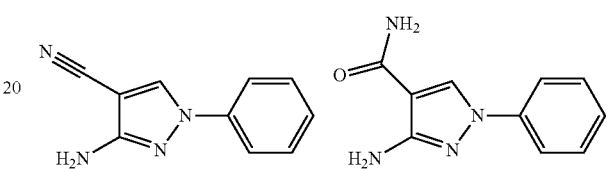

Step 2. 3-amino-1-phenyl-1H-pyrazole-4-carbonitrile and 3-amino-1-phenyl-1H-pyrazole-4-carboxamide {[(4-cyano-1-phenyl-1H-pyrazol-3-yl)amino]methylene}malononitrile (1.07 g, 4.11 mmol) was stirred in refluxing dioxane (80 mL)/2 N HCl (80 mL) for 3 days. Room temperature was attained and the products extracted into EtOAc (×2). The combined organic extracts were washed with brine, dried over MgSO$_4$ and concentrated in vacuo. Purification of the residue by MPLC (12-100% EtOAc-hexanes followed by 0-10% MeOH-EtOAc) gave 3-amino-1-phenyl-1H-pyrazole-4-carbonitrile as a beige solid (A) and 3-amino-1-phenyl-1H-pyrazole-4-carboxamide as a brown solid (B).

A—LRMS (APCI) calc'd for ($C_{10}H_9N_4$) [M+H]$^+$: 185, Found: 185.

B—LRMS (APCI) calc'd for ($C_{10}H_{11}N_4O$) [M+H]$^+$: 203, Found: 203.

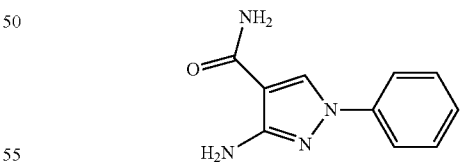

Step 3. 3-3-amino-1-phenyl-1H-pyrazole-4-carboxamide 3-amino-1-phenyl-1H-pyrazole-4-carbonitrile (0.34 g, 1.846 mmol) was stirred in 95% H$_2$SO$_4$ (10 mL) at 50° C. for 3 hours. Room temperature was attained, water was added and the products extracted into EtOAc (×3). The aqueous phase was neutralised with 2 N NaOH and the products extracted into DCM (×2) followed by 20% MeOH-DCM (×4). The combined organic extracts were dried over $MgSO_4$ and concentrated in vacuo. The residue was triturated in EtOAc to give 3-amino-1-phenyl-1H-pyrazole-4-carboxamide as a pale yellow solid.

LRMS (APCI) calc'd for $(C_{10}H_{11}N_4O)$ [M+H]$^+$: 203, Found: 203.

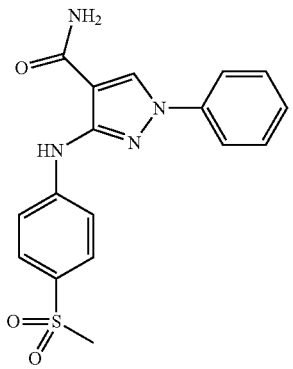 [SMILES: CS(=O)(=O)c1ccc(Nc2nn(-c3ccccc3)cc2C(N)=O)cc1]

Step 4. 3-{[4-(methylsulfonyl)phenyl]amino}-1-phenyl-1H-pyrazole-4-carboxamide 3-amino-1-phenyl-1H-pyrazole-4-carboxamide (50 mg, 0.247 mmol), 4-bromophenyl methyl sulfone (58.1 mg, 0.247 mmol), $Pd_2$ $dba_3$ (22.64 mg, 0.025 mmol), $K_2CO_3$ (37.6 mg, 0.272 mmol) and X-Phos (58.9 mg, 0.124 mmol) were added to a 5 mL microwave vial. Degassed EtOH (0.75 mL) was added and the vial evacuated and back-filled with $N_2$ (×3). The resulting mixture was stirred at 100° C. for 4 hours. Room temperature was attained, MeOH was added and the solvent removed in vacuo while loading onto silica. Purification of the residue by MPLC (0-6% MeOH—$CHCl_3$) gave 3-{[4-(methylsulfonyl)phenyl]amino}-1-phenyl-1H-pyrazole-4-carboxamide as a pale yellow solid after triturating in DCM.

LRMS (APCI) calc'd for $(C_{17}H_{17}N_4O_3S)$ [M+H]$^+$: 357, Found: 357. JAK2 $IC_{50}$=170 nM.

Additional analogues were prepared using procedures similar to those described in the above examples.

TABLE 1

| Example # | Structure | Compound Name | Characterization [M + H]$^+$ | JAK2 $IC_{50}$ (nM) |
|---|---|---|---|---|
| 2 | 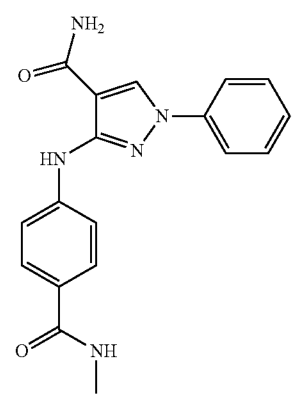 [SMILES: CNC(=O)c1ccc(Nc2nn(-c3ccccc3)cc2C(N)=O)cc1] | 3-({4-[(methylamino)carbonyl]phenyl}amino)-1-phenyl-1H-pyrazole-4-carboxamide | Calc'd 336, found 336 | 160 |
| 3 | 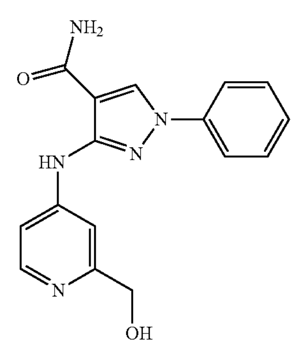 [SMILES: NC(=O)c1cn(-c2ccccc2)nc1Nc1ccnc(CO)c1] | 3-{[2-(hydroxymethyl)pyridin-4-yl]amino}-1-phenyl-1H-pyrazole-4-carboxamide | Calc'd 310, found 310 | 860 |

EXAMPLE 4

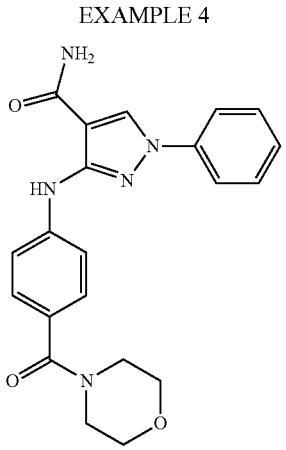

3-{[4-(morpholin-4-ylcarbonyl)phenyl]amino}-1-phenyl-1H-pyrazole-4-carboxamide

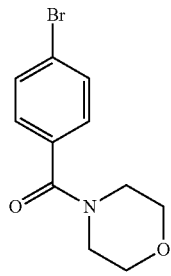

Step 1. 4(4-bromobenzoyl)morpholine 4-bromobenzoyl chloride (5 g, 22.78 mmol) was taken up in THF (75 mL) and cooled to 0° C. A solution of morpholine (2.084 mL, 23.92 mmol) and DIPEA (4.38 mL, 25.06 mmol) in THF (25 mL) was added dropwise and the resulting mixture stirred at 0° C. for 3 hours. Water as added and the products extracted into EtOAc (×2). The combined organic extracts were washed with brine, dried over MgSO$_4$ and concentrated in vacuo to give 4-(4-bromobenzoyl)morpholine as a pale yellow gum.

LRMS (APCI) calc'd for $(C_{11}H_{13}BrNO_2)$ [M+H]$^+$: 270, 272, Found: 270, 272.

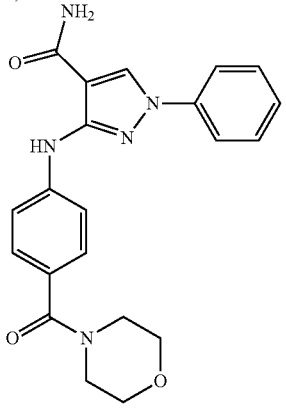

Step 2. 3-{[4-(morpholin-4-ylcarbonyl)phenyl]amino}-1-phenyl-1H-pyrazole-4-carboxamide 3-{[4-(morpholin-4-ylcarbonyl)phenyl]amino}-1-phenyl-1H-pyrazole-4-carboxamide was prepared according to the general procedure in Example 1 Step 4 using 3-amino-1-phenyl-1H-pyrazole-4-carboxamide (52 mg, 0.257 mmol) and 4-(4-bromobenzoyl)morpholine (69.5 mg, 0.257 mmol) as the starting materials.

LRMS (APCI) calc'd for $(C_{21}H_{22}N_5O_3)$ [M+H]$^+$: 392, Found: 392. JAK2 IC$_{50}$=94 nM.

EXAMPLE 5

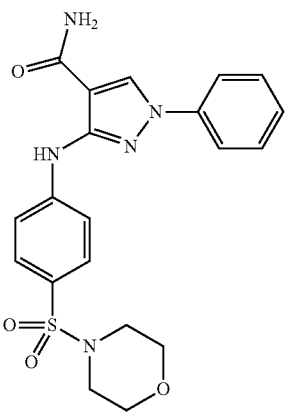 [SMILES: NC(=O)c1cn(-c2ccccc2)nc1Nc1ccc(S(=O)(=O)N2CCOCC2)cc1]

3-{[4-(morpholin-4-ylsulfonyl)phenyl]amino}-1-phenyl-1H-pyrazole-4-carboxamide

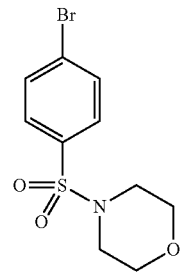 [SMILES: O=S(=O)(c1ccc(Br)cc1)N1CCOCC1]

Step 1. 4-[(4-bromophenyl)sulfonyl]morpholine

Morpholine (58.2 mg, 0.668 mmol) and triethylamine (116 µL, 0.835 mmol) were placed in a round-bottom flask with a stir bar. Dry dichloromethane (5870 µL) was then added and the solution cooled to 0° C. 4-bromobenzenesulfonyl chloride (150 mg, 0.556 mmol) was added and the reaction was allowed to warm to room temperature overnight. It was quenched with water and extracted in ethyl acetate. The organic layers were washed with aqueous sodium bicarbonate, dried over magnesium sulfate, filtered, and concentrated under reduced pressure to give 4-[(4-bromophenyl)sulfonyl]morpholine as a white solid.

LRMS (APCI) calc'd for $(C_{11}H_{13}BrNO_2)$ [M+H]$^+$: 270, 272, Found: 270, 272.

Step 2. 3-{[4-(morpholin-4-ylsulfonyl)phenyl]amino}-1-phenyl-1H-pyrazole-4-carboxamide 3-{[4-(morpholin-4-ylsulfonyl)phenyl]amino}-1-phenyl-1H-pyrazole-4-carboxamide was prepared according to the general procedure in Example 1 Step 4 using 3-amino-1-phenyl-1H-pyrazole-4-carboxamide (34 mg, 0.168 mmol) and 4-[(4-bromophenyl)sulfonyl]morpholine (51.5 mg, 0.168 mmol) as the starting materials.

LRMS (APCI) calc'd for ($C_{20}H_{22}N_5O_4S$) [M+H]$^+$: 428, Found: 428. JAK2 $IC_{50}$=63 nM.

Additional analogues were prepared using procedures similar to those described in the above examples.

Step 1. 3-anilino-1-phenyl-1H-pyrazole-4-carbonitrile and 3-amino-1-phenyl-1H-pyrazole-4-carbonitrile 3-amino-1H-pyrazole-4-carbonitrile (200 mg, 1.850 mmol), copper(II) acetate (504 mg, 2.78 mmol), phenylboronic acid (451 mg, 3.70 mmol) and pyridine (0.599 mL, 7.40 mmol) were stirred in DCM (20 mL) at room temperature overnight. 2 N HCl was added and the products extracted in EtOAc (×2). The combined organic extracts were washed with brine, dried over $MgSO_4$ and concentrated in vacuo. Purification of the residue by MPLC (2-30% EtOAc-hexanes) gave 3-anilino-1-phenyl-1H-pyrazole-4-carbonitrile (A) as a yellow solid and 3-amino-1-phenyl-1H-pyrazole-4-carbonitrile (B) as a pale yellow solid. 5-amino-1-phenyl-1H-pyrazole-4-carbonitrile was also isolated.

A—LRMS (APCI) calc'd for ($C_{16}H_{13}N_4$) [M+H]$^+$: 261, Found: 261.

B—LRMS (APCI) calc'd for ($C_{10}H_9N_4$) [M+H]$^+$: 185, Found: 185.

TABLE 2

| Example # | Structure | Compound Name | Characterization [M + H]$^+$ | JAK2 $IC_{50}$ (nM) |
|---|---|---|---|---|
| 6 | 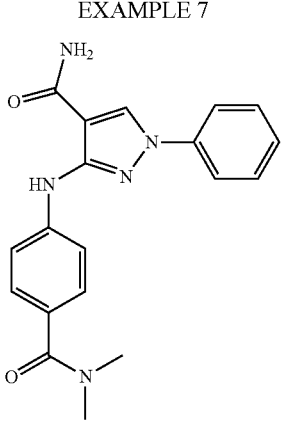 | 3-({4-[(dimethylamino)sulfonyl]phenyl}amino)-1-phenyl-1H-pyrazole-4-carboxamide | Calc'd 386, found 386 | 42 |

EXAMPLE 7

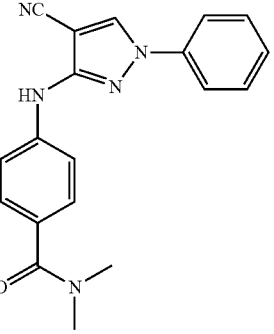

3-({4-[(dimethylamino)carbonyl]phenyl}amino)-1-phenyl-1H-pyrazole-4-carboxamide

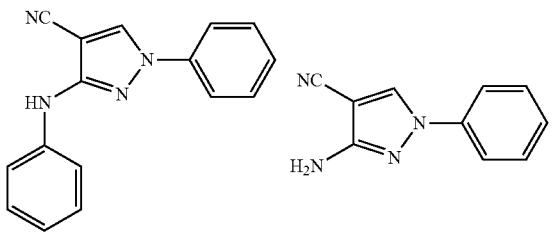

Step 2. 4-[(4-cyano-1-phenyl-1H-pyrazol-3-yl)amino]-N,N-dimethylbenzamide 3-amino-1-phenyl-1H-pyrazole-4-carbonitrile (60 mg, 0.326 mmol), 4-bromo-N,N-dimethylbenzamide (74.3 mg, 0.326 mmol), $Pd_2dba_3$ (14.91 mg, 0.016 mmol), $K_2CO_3$ (49.5 mg, 0.358 mmol) and X-Phos (38.8 mg, 0.081 mmol) were added to a 5 mL microwave vial. Tert-amyl alcohol (1 mL)

was added and the vial was evacuated and back-filled with $N_2$ (×3). The resulting mixture was stirred at 100° C. overnight. Room temperature was attained, EtOAc was added and the solvent removed in vacuo while loading onto silica. Purification of the residue by MPLC (0-10% MeOH—$CHCl_3$) followed by MPLC (12-100% EtOAc-hexanes) gave 4-[(4-cyano-1-phenyl-1H-pyrazol-3-yl)amino]-N,N-dimethylbenzamide as a pale yellow solid.

LRMS (APCI) calc'd for $(C_{19}H_{18}N_5O)$ [M+]$^+$: 332, Found: 332.

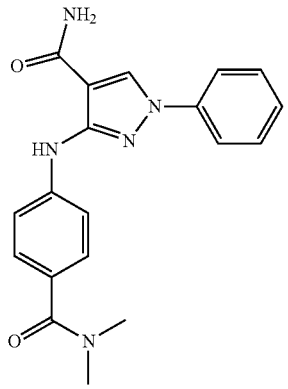 [SMILES: CN(C)C(=O)c1ccc(Nc2nn(-c3ccccc3)cc2C(N)=O)cc1]

Step 3. 3-({4-[(dimethylamino)carbonyl]phenyl}amino)-1-phenyl-1H-pyrazole-4-carboxamide 4-[(4-cyano-1-phenyl-1H-pyrazol-3-yl)amino]-N,N-dimethylbenzamide (83 mg, 0.250 mmol) and 5 N sodium hydroxide (0.351 mL, 1.753 mmol) were taken up in DMSO (1 mL)/EtOH (1 mL) and warmed to 60° C. Hydrogen peroxide (0.329 mL, 3.76 mmol) was added dropwise and stirring continued at 60° C. for 15 minutes. Room temperature was attained, water was added and the products extracted into EtOAc (×2). The combined organic extracts were washed with brine (×2), dried over $MgSO_4$ and concentrated in vacuo. Purification of the residue by MPLC (25-100% EtOAc-hexanes followed by 0-10% MeOH-EtOAc followed by 15% MeOH—$CHCl_3$) gave 3-({4-[(dimethylamino)carbonyl]phenyl}amino)-1-phenyl-1H-pyrazole-4-carboxamide as a pale yellow solid.

LRMS (APCI) calc'd for $(C_{19}H_{20}N_5O_2)$ [M+H]$^+$: 350, Found: 350. JAK2 $IC_{50}$=56 nM.

EXAMPLE 8

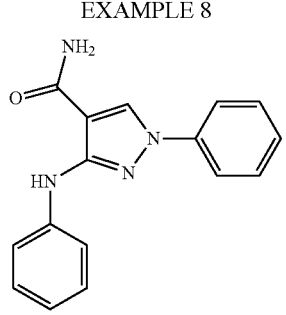

3-anilino-1-phenyl-1H-pyrazole-4-carboxamide 3-anilino-1-phenyl-1H-pyrazole-4-carboxamide was prepared according to the general procedure in Example 7 Step 3 using 3-anilino-1-phenyl-1H-pyrazole-4-carbonitrile (10 mg, 0.038 mmol) as the starting material.

LRMS (APCI) calc'd for $(C_{16}H_{15}N_4O)$ [M+H]$^+$: 279, Found: 279. JAK2 $IC_{50}$=480 nM.

EXAMPLE 9

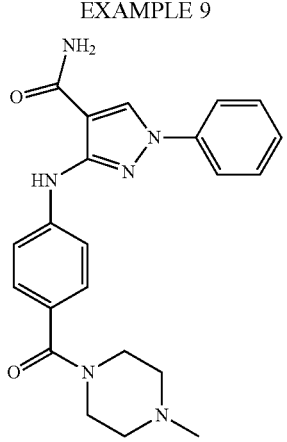

3-({4-[(4-methylpiperazin-1-yl)carbonyl]phenyl}amino)-1-phenyl-1H-pyrazole-4-carboxamide

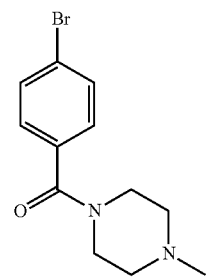 [SMILES: CN1CCN(C(=O)c2ccc(Br)cc2)CC1]

Step 1. 4-bromobenzo 1-4-methylpiperazine 1-(4-bromobenzoyl)-4-methylpiperazine was prepared according to the general procedure in Example 4 Step 1 using 4-bromobenzoyl chloride (1 g, 4.56 mmol) and 1-methylpiperazine (0.532 mL, 4.78 mmol) as the starting materials.

LRMS (APCI) calc'd for $(C_{12}H_{16}BrN_2O)$ [M+H]$^+$: 283, 285, Found: 283, 285.

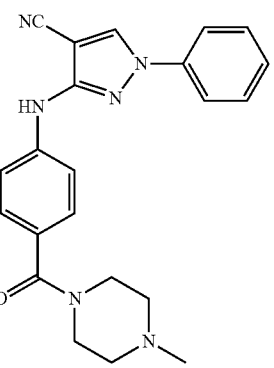

Step 2. 3-({4-[(4-methylpiperazin-1-yl)carbonyl]phenyl}amino)-1-phenyl-1H-pyrazole-4-carbonitrile 3-({4-[(4-methylpiperazin-1-yl)carbonyl]phenyl}amino)-1-phenyl-1H-pyrazole-4-carbonitrile was prepared according to the general procedure in Example 7 Step 2 using 3-amino-1-phenyl-1H-pyrazole-4-carbonitrile (50 mg, 0.271 mmol) and 1-(4-bromobenzoyl)-4-methylpiperazine (77 mg, 0.271 mmol) as the starting materials.

LRMS (APCI) calc'd for ($C_{12}H_{23}N_6O$) [M+H]$^+$: 387, Found: 387.

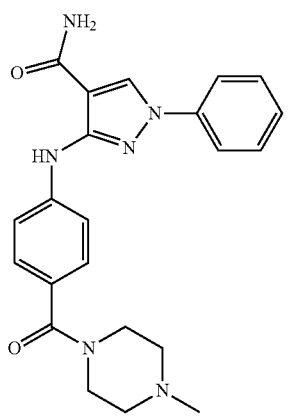 [SMILES: CN1CCN(C(=O)c2ccc(Nc3nn(-c4ccccc4)cc3C(N)=O)cc2)CC1]

Step 3. 3-({4-[(4-methylpiperazin-1-yl)carbonyl]phenyl}amino)-1-phenyl-1H-pyrazole-4-carboxamide 3-({4-[(4-methylpiperazin-1-yl)carbonyl]phenyl}amino)-1-phenyl-1H-pyrazole-4-carboxamide was prepared according to the general procedure in Example 7 Step 3 using 3-({4-[(4-methylpiperazin-1-yl)carbonyl]phenyl}amino)-1-phenyl-1H-pyrazole-4-carbonitrile (90 mg, 0.233 mmol) as the starting material.

LRMS (APCI) calc'd for ($C_{22}H_{25}N_6O_2$) [M+H]$^+$: 405, Found: 405. JAK2 $IC_{50}$=38 nM.

Additional analogues were prepared using procedures similar to those described in the above examples.

EXAMPLE 11

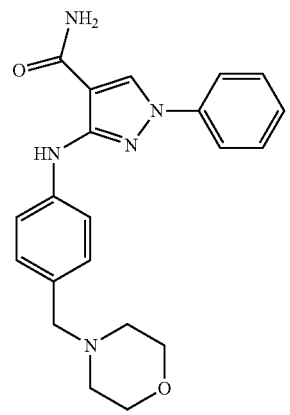 [SMILES: NC(=O)c1cn(-c2ccccc2)nc1Nc1ccc(CN2CCOCC2)cc1]

3-{[4-(morpholin-4-ylmethyl)phenyl]amino}-1-phenyl-1H-pyrazole-4-carboxamide

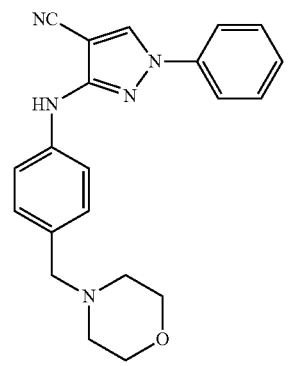 [SMILES: N#Cc1cn(-c2ccccc2)nc1Nc1ccc(CN2CCOCC2)cc1]

Step 1. 3-{[4-(morpholin-4-ylmethyl)phenyl]amino}-1-phenyl-1H-pyrazole-4-carbonitrile 3-amino-1-phenyl-1H-pyrazole-4-carbonitrile (100 mg, 0.543 mmol), 4-(4-iodobenzyl)morpholine (165 mg, 0.543 mmol), $Pd_2dba_3$ (24.86 mg, 0.027 mmol), $K_2CO_3$ (83 mg, 0.597 mmol) and X-Phos (64.7 mg, 0.136 mmol) were added to a 5 mL microwave vial. Degassed tert-amyl alcohol (0.8 mL) was added and the vial was evacuated and back-filled

TABLE 3

| Example # | Structure | Compound Name | Characterization [M + H]$^+$ | JAK2 IC$_{50}$ (nM) |
|---|---|---|---|---|
| 10 | NH$_2$ structure | 3-({4-[(1,1-dioxidothiomorpholin-4-yl)carbonyl]phenyl}amino)-1-phenyl-1H-pyrazole-4-carboxamide | Calc'd 440, found 440 | 13 | with N₂ (×3). The resulting mixture was stirred at 100° C. for 24 hours. Room temperature was attained, MeOH was added and the solvent removed in vacuo while loading onto silica. Purification of the residue by MPLC (0-15% MeOH—CHCl₃) gave 3-{[4-(morpholin-4-ylmethyl)phenyl]amino}-1-phenyl-1H-pyrazole-4-carbonitrile as a beige solid.

LRMS (APCI) calc'd for (C₂₁H₂₂N₅O) [M+H]⁺: 360, Found: 360.

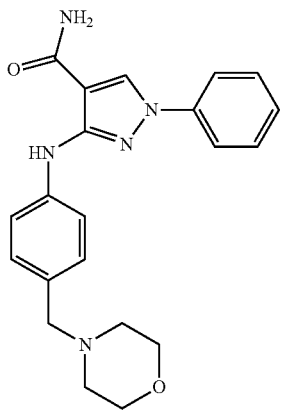 [SMILES: NC(=O)c1cn(-c2ccccc2)nc1Nc1ccc(CN2CCOCC2)cc1]

Step 2. 3-{[4-(morpholin-4-ylmethyl)phenyl]amino}-1-phenyl-1H-pyrazole-4-carboxamide 3-{[4-(morpholin-4-ylmethyl)phenyl]amino}-1-phenyl-1H-pyrazole-4-carboxamide was prepared according to the general procedure in Example 7 Step 3 using 3-{[4-(morpholin-4-ylmethyl)phenyl]amino}-1-phenyl-1H-pyrazole-4-carbonitrile (81 mg, 0.225 mmol) as the starting material.

LRMS (APCI) calc'd for (C₁₇H₁₅N₄O—loss of amino fragment) [M+H]⁺: 291, Found: 291. JAK2 IC₅₀=49 nM.

EXAMPLE 12

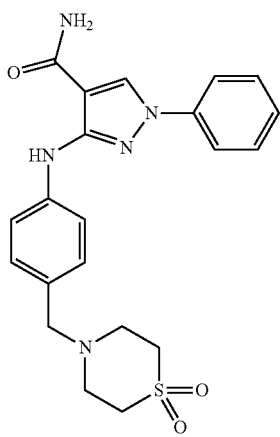 [SMILES: NC(=O)c1cn(-c2ccccc2)nc1Nc1ccc(CN2CCS(=O)(=O)CC2)cc1]

3-({4-[(1,1-dioxidothiomorpholin-4-yl)methyl]phenyl}amino)-1-phenyl-1H-pyrazole-4-carboxamide

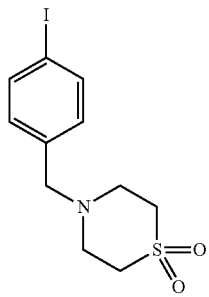 [SMILES: O=S1(=O)CCN(Cc2ccc(I)cc2)CC1]

Step 1. 4-(4-iodobenzyl)thiomorpholine 1,1-dioxide 1-(bromomethyl)-4-iodobenzene (1 g, 3.37 mmol), thiomorpholine 1,1-dioxide (0.546 g, 4.04 mmol) and DIPEA (0.882 mL, 5.05 mmol) were stirred in THF (15 mL) at room temperature overnight. The solvent was removed in vacuo while loading onto silica. Purification of the residue by MPLC (12-100% EtOAc-hexanes) gave 4-(4-iodobenzyl)thiomorpholine 1,1-dioxide as a white solid.

LRMS (APCI) calc'd for (C₁₁H₁₅INO₂S) [M+H]⁺: 352, Found: 352.

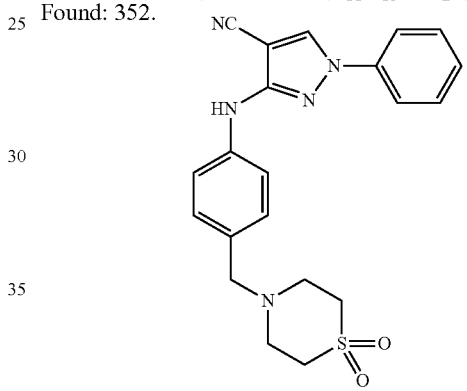

Step 2. 3-({4-[(1,1-dioxidothiomorpholin-4-yl)methyl]phenyl}amino)-1-phenyl-1H-pyrazole-4-carbonitrile 3-({4-[(1,1-dioxidothiomorpholin-4-yl)methyl]phenyl}amino)-1-phenyl-1H-pyrazole-4-carbonitrile was prepared according to the general procedure in Example 11 Step 1 using 3-amino-1-phenyl-1H-pyrazole-4-carbonitrile (100 mg, 0.543 mmol) and 4-(4-iodobenzyl)thiomorpholine 1,1-dioxide (191 mg, 0.543 mmol) as the starting materials.

LRMS (APCI) calc'd for (C₁₇H₁₃N₄—loss of amino fragment) [M+H]⁺: 272, Found: 272.

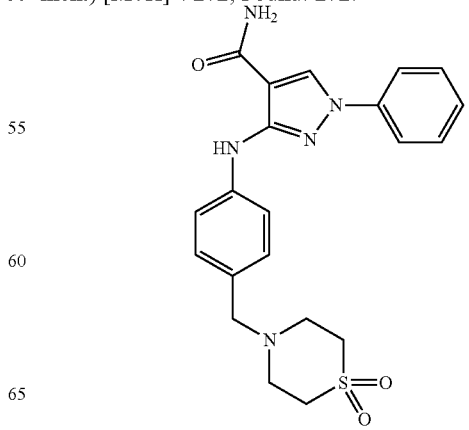

Step 3. 3-({4-[(1,1-dioxidothiomorpholin-4-yl)methyl]phenyl}amino)-1-phenyl-1H-pyrazole-4-carboxamide 3-({4-[(1,1-dioxidothiomorpholin-4-yl)methyl]phenyl}amino)-1-phenyl-1H-pyrazole-4-carboxamide was prepared according to the general procedure in Example 7 Step 3 using 3-({4-[(1,1-dioxidothiomorpholin-4-yl)methyl]phenyl}amino)-1-phenyl-1H-pyrazole-4-carbonitrile (79 mg, 0.194 mmol) as the starting material.

LRMS (APCI) calc'd for ($C_{21}H_{24}N_5O_3S$) [M+H]$^+$: 426, Found: 426. JAK2 IC$_{50}$=36 nM.

Additional analogues were prepared using procedures similar to those described in the above examples.

Step 1. 2-(4-iodophenyl)propan-2-ol

Methyl 4-iodobenzoate (10 g, 38.2 mmol) was taken up in THF (100 mL) and cooled to 0° C. Methylmagnesium bromide (38.2 ml, 114 mmol) was added dropwise and stirring at 0° C. continued for 30 minutes. Saturated NH$_4$Cl was added and the products extracted into EtOAc (×2). The combined organic extracts were washed with brine, dried over MgSO$_4$ and concentrated in vacuo. Purification of the residue by MPLC (6-50% EtOAc-hexanes) gave 2-(4-iodophenyl)propan-2-ol as a yellow oil.

LRMS (APCI) calc'd for ($C_9H_{10}I$—loss of water) [M+H]$^+$: 245, Found: 245.

TABLE 4

| Example # | Structure | Compound Name | Characterization [M + H]$^+$ | JAK2 IC$_{50}$ (nM) |
|---|---|---|---|---|
| 13 | 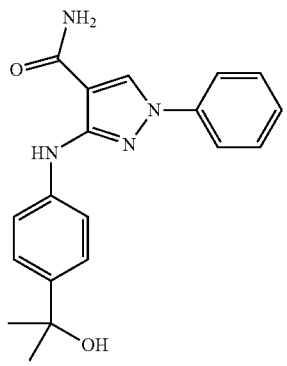 [SMILES: CC(C)(O)c1ccc(Nc2nn(-c3ccccc3)cc2C(N)=O)cc1] | 3-({4-[(dimethylamino)methyl]phenyl}amino)-1-phenyl-1H-pyrazole-4-carboxamide | Calc'd 291 (loss of amino fragment), found 291 | 36 |

EXAMPLE 14

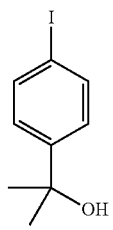

3-{[4-(1-hydroxy-1-methylethyl)phenyl]amino}-1-phenyl-1H-pyrazole-4-carboxamide

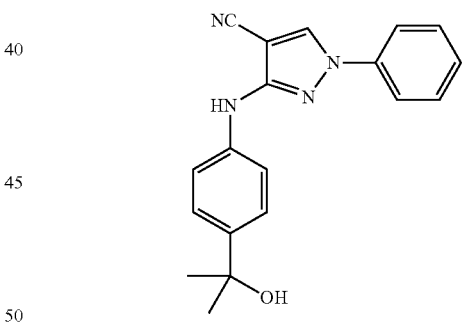

Step 2. 3-{[4-(1-hydroxy-1-methylethyl)phenyl]amino}-1-phenyl-1H-pyrazole-4-carbonitrile 3-{[4-(1-hydroxy-1-methylethyl)phenyl]amino}-1-phenyl-1H-pyrazole-4-carbonitrile was prepared according to the general procedure in Example 11 Step 1 using 3-amino-1-phenyl-1H-pyrazole-4-carbonitrile (70 mg, 0.380 mmol) and 2-(4-iodophenyl)propan-2-ol (100 mg, 0.380 mmol) as the starting materials.

LRMS (APCI) calc'd for ($C_{19}H_{19}N_4O$) [M+H]$^+$: 319, Found: 319.

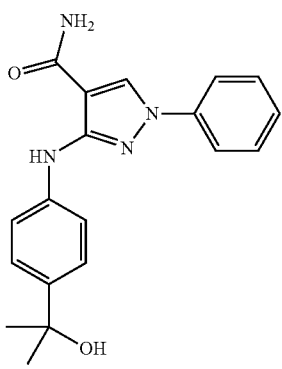 [SMILES: CC(C)(O)c1ccc(Nc2nn(-c3ccccc3)cc2C(N)=O)cc1]

Step 3. 3-{[4-(1-hydroxy-1-methylethyl)phenyl]amino}-1-phenyl-1H-pyrazole-4-carboxamide 3-{[4-(1-hydroxy-1-methylethyl)phenyl]amino}-1-phenyl-1H-pyrazole-4-carboxamide was prepared according to the general procedure in Example 7 Step 3 using 3-{[4-(1-hydroxy-1-methylethyl)phenyl]amino}-1-phenyl-1H-pyrazole-4-carbonitrile (36 mg, 0.113 mmol) as the starting material.

LRMS (APCI) calc'd for $(C_{19}H_{21}N_4O_2)$ $[M+H]^+$: 337, Found: 337. JAK2 $IC_{50}$=81 nM.

EXAMPLE 15

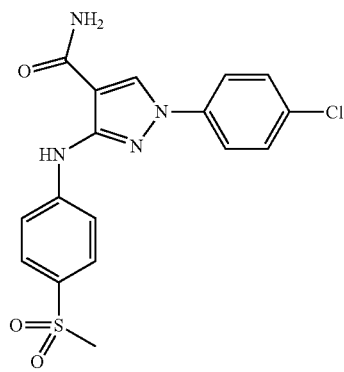 [SMILES: CS(=O)(=O)c1ccc(Nc2nn(-c3ccc(Cl)cc3)cc2C(N)=O)cc1]

1-(4-chlorophenyl)-3-{[4-(methylsulfonyl)phenyl]amino}-1H-pyrazole-4-carboxamide

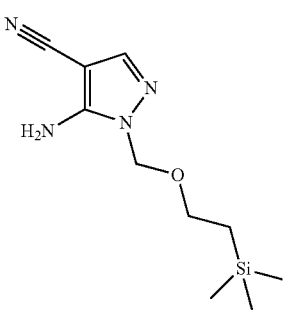

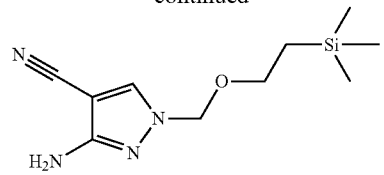

Step 1. 5-amino-1-{[2-(trimethylsilyl)ethoxy]methyl}-1H-pyrazole-4-carbonitrile and 3-amino-1-{[2-(trimethylsilyl)ethoxy]methyl}-1H-pyrazole-4-carbonitrile 3-amino-1H-pyrazole-4-carbonitrile (10 g, 93 mmol) and $K_2CO_3$ (19.18 g, 139 mmol) were taken up in DMF (60 mL). SEM-Cl (19.69 mL, 111 mmol) was added at a fast dropwise rate (exotherm) and the resulting mixture stirred at room temperature overnight. Water was added and the products extracted into EtOAc (×2). The combined organic extracts were washed with brine, dried over $MgSO_4$ and concentrated in vacuo. Purification of the residue by MPLC (6-50% EtOAc-hexanes) gave 5-amino-1-{[2-(trimethylsilyl)ethoxy]methyl}-1H-pyrazole-4-carbonitrile (A) as a pale yellow solid and 3-amino-1-{[2-(trimethylsilyl)ethoxy]methyl}-1H-pyrazole-4-carbonitrile (B) as a yellow oily solid.

A—$^1$H NMR (600 MHz, d6-DMSO): δ 7.54 (s, 1 H), 6.77 (s, 2 H), 5.21 (s, 2 H), 3.49 (m, 2 H), 0.78 (m, 2 H), 0.08 (s, 9 H).

B—$^1$H NMR (600 MHz, d6-DMSO): δ 8.24 (s, 1 H), 5.60 (s, 2 H), 5.11 (s, 2 H), 3.47 (m, 2 H), 0.79 (m, 2 H), 0.07 (s, 9 H).

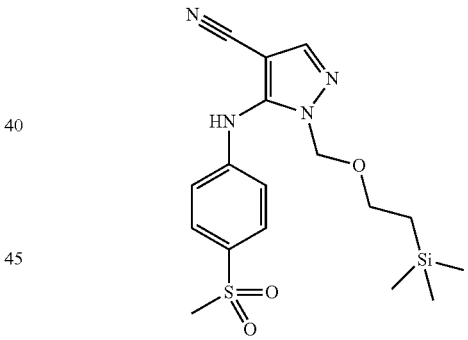

Step 2. 5-{[4-(methylsulfonyl)phenyl]amino}-1-{[2-(trimethylsilyl)ethoxy]methyl}-1H-pyrazole-4-carbonitrile 5-amino-1-{[2-(trimethylsilyl)ethoxy]methyl}-1H-pyrazole-4-carbonitrile (1.27 g, 5.33 mmol), 4-bromophenyl methyl sulfone (1.253 g, 5.33 mmol), $Pd_2$ $dba_3$ (0.244 g, 0.266 mmol), $K_2CO_3$ (0.810 g, 5.86 mmol) and X-Phos (0.635 g, 1.332 mmol) were taken up in tert-amyl alcohol (15 mL). The flask was evacuated and back-filled with $N_2$ (×3) and the resulting mixture was stirred at 100° C. overnight. MeOH was added and the solvent removed in vacuo while loading onto silica. Purification of the residue by MPLC (12-100% EtOAc-hexanes) followed by MPLC (6-100% EtOAc-hexanes) gave 5-{[4-(methylsulfonyl)phenyl]amino}-1-{[2-(trimethylsilyl)ethoxy]methyl}-1H-pyrazole-4-carbonitrile as a hygroscopic yellow solid.

¹H NMR (600 MHz, d6-DMSO): δ 9.40 (s, 1 H), 8.10 (s, 1 H), 7.75 (m, 2 H), 6.98 (m, 2 H), 5.38 (s, 2 H), 3.46 (m, 2 H), 3.09 (s, 3 H), 0.74 (m, 2 H), 0.17 (s, 9 H).

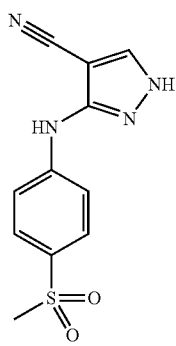

Step 3. 3-{[4-(methylsulfonyl)phenyl]amino}-1H-pyrazole-4-carbonitrile

5-{[4-(methylsulfonyl)phenyl]amino}-1-{[2-(trimethylsilyl)ethoxy]methyl}-1H-pyrazole-4-carbonitrile (0.82 g, 2.089 mmol) was stirred in ethanol (40 mL)/2 N HCl (40 mL) at 80° C. for 2 hours. Room temperature was attained, saturated NaHCO₃ was added and the products extracted into EtOAc (×2). The combined organic extracts were washed with brine, dried over MgSO₄ and concentrated in vacuo to give 3-{[4-(methylsulfonyl)phenyl]amino}-1H-pyrazole-4-carbonitrile as a pale yellow solid.

LRMS (APCI) calc'd for $(C_{11}H_{11}N_4O_2S)$ [M+H]⁺: 263, Found: 263.

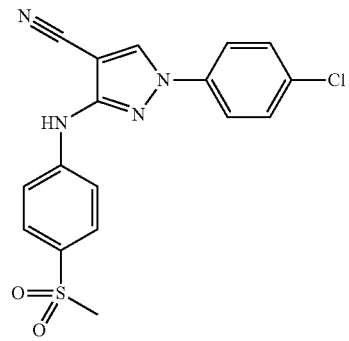 [SMILES: CS(=O)(=O)c1ccc(Nc2nn(-c3ccc(Cl)cc3)cc2C#N)cc1]

Step 4. 1-(4-chlorophenyl)-3-{[4-(methylsulfonyl)phenyl]amino}-1H-pyrazole-4-carbonitrile 3-{[4-(methylsulfonyl)phenyl]amino}-1H-pyrazole-4-carbonitrile (64 mg, 0.244 mmol), copper(II) acetate (66.5 mg, 0.366 mmol), (4-chlorophenyl)boronic acid (76 mg, 0.488 mmol) and pyridine (0.079 mL, 0.976 mmol) were stirred in DCM (8 mL) at room temperature overnight. 2 N HCl was added and the products extracted into EtOAc (×2). The combined organic extracts were washed with brine, dried over MgSO₄ and concentrated in vacuo. Purification of the residue twice by MPLC (5-60% EtOAc-hexanes) gave 1-(4-chlorophenyl)-3-{[4-(methylsulfonyl)phenyl]amino}-1H-pyrazole-4-carbonitrile as a white solid. 1-(4-chlorophenyl)-5-{[4-(methylsulfonyl)phenyl]amino}-1H-pyrazole-4-carbonitrile was also isolated.

LRMS (APCI) calc'd for $(C_{17}H_{14}ClN_4O_2S)$ [M+H]⁺: 373, 375, Found: 373, 375.

Step 5. 1-(4-chlorophenyl)-3-{[4-(methylsulfonyl)phenyl]amino}-1H-pyrazole-4-carboxamide 1-(4-chlorophenyl)-3-{[4-(methylsulfonyl)phenyl]amino}-1H-pyrazole-4-carboxamide was prepared according to the general procedure in Example 7 Step 3 using 1-(4-chlorophenyl)-3-{[4-(methylsulfonyl)phenyl]amino}-1H-pyrazole-4-carbonitrile (27 mg, 0.072 mmol) as the starting material.

LRMS (APCI) calc'd for $(C_{17}H_{16}ClN_4O_3S)$ [M+H]⁺: 391, 393, Found: 391, 393. JAK2 IC₅₀=290 nM.

Additional analogues were prepared using procedures similar to those described in the above examples.

TABLE 5

| Example # | Structure | Compound Name | Characterization [M + H]⁺ | JAK2 IC₅₀ (nM) |
|---|---|---|---|---|
| 16 | (structure) | 1-[4-(methylsulfonyl)phenyl]-3-{[4-(methylsulfonyl)phenyl]amino}-1H-pyrazole-4-carboxamide | Calc'd 435, found 435 | 48 |

TABLE 5-continued

| Example # | Structure | Compound Name | Characterization [M + H]+ | JAK2 IC$_{50}$ (nM) |
|---|---|---|---|---|
| 17 | 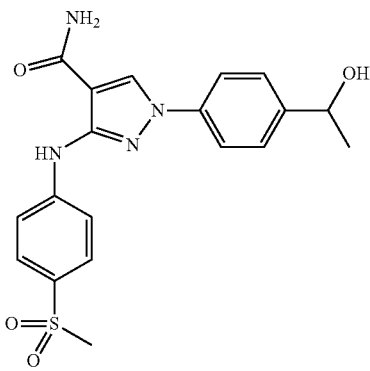 [SMILES: CC(O)c1ccc(-n2cc(C(N)=O)c(Nc3ccc(S(C)(=O)=O)cc3)n2)cc1] | 1-(4-tert-butylphenyl)-3-{[4-(methylsulfonyl)phenyl]amino}-1H-pyrazole-4-carboxamide | Calc'd 413, found 413 | 8.1 |

EXAMPLE 18

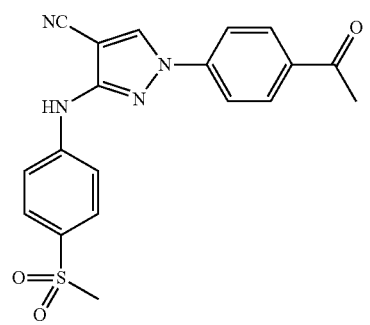 [SMILES: CC(=O)c1ccc(-n2cc(C#N)c(Nc3ccc(S(C)(=O)=O)cc3)n2)cc1]

1-[4-(1-hydroxyethyl)phenyl]-3-{[4-(methylsulfonyl)phenyl]amino}-1H-pyrazole-4-carboxamide

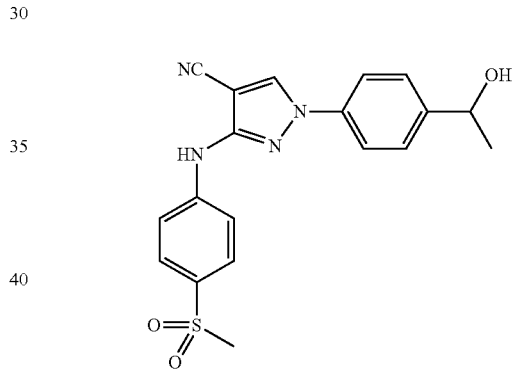

Step 1. 1-(4-acetylphenyl)-3-{[4-(methylsulfonyl)phenyl]amino}-1H-pyrazole-4-carbonitrile 1-(4-acetylphenyl)-3-{[4-(methylsulfonyl)phenyl]amino}-1H-pyrazole-4-carbonitrile was prepared according to the general procedure in Example 15 Step 4 using 3-{[4-(methylsulfonyl)phenyl]amino}-1H-pyrazole-4-carbonitrile (0.24 g, 0.915 mmol) and (4-acetylphenyl)boronic acid (0.300 g, 1.830 mmol) as the starting materials.

LRMS (APCI) calc'd for ($C_{19}H_{17}N_4O_3S$) [M+H]+: 381, Found: 381.

Step 2. 1-[4-(1-hydroxyethyl)phenyl]-3-{[4-(methylsulfonyl)phenyl]amino}-1H-pyrazole-4-carbonitrile 1-(4-acetylphenyl)-3-{[4-(methylsulfonyl)phenyl]amino}-1H-pyrazole-4-carbonitrile (30 mg, 0.079 mmol) and sodium borohydride (5.97 mg, 0.158 mmol) were stirred in dioxane (1 mL) at 60° C. overnight. Additional sodium borohydride (5.97 mg, 0.158 mmol) was added and stirring at 60° C. continued for 24 hours. Room temperature was attained, water was added and the products extracted into EtOAc (×2). The combined organic extracts were washed with brine, dried over MgSO$_4$ and concentrated in vacuo. The residue was triturated in DCM to give 1-[4-(1-hydroxyethyl)phenyl]-3-{[4-(methylsulfonyl)phenyl]amino}-1H-pyrazole-4-carbonitrile as a white solid.

LRMS (APCI) calc'd for ($C_{19}H_{19}N_4O_3S$) [M+H]+: 383, Found: 383.

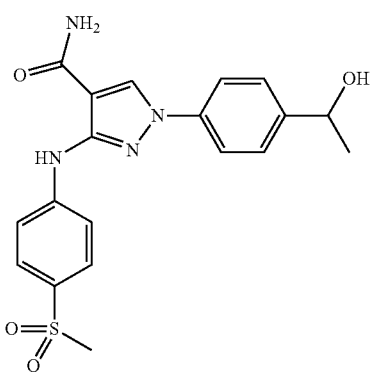 [SMILES: CC(O)c1ccc(-n2cc(C(N)=O)c(Nc3ccc(S(C)(=O)=O)cc3)n2)cc1]

Step 3. 1-[4-(1-hydroxyethyl)phenyl]-3-{[4-(methylsulfonyl)phenyl]amino}-1H-pyrazole-4-carboxamide 1-[4-(1-hydroxyethyl)phenyl]-3-{[4-(methylsulfonyl)phenyl]amino}-1H-pyrazole-4-carboxamide was prepared according to the general procedure in Example 7 Step 3 using 1-[4-(1-hydroxyethyl)phenyl]-3-{[4-(methylsulfonyl)phenyl]amino}-1H-pyrazole-4-carbonitrile (15 mg, 0.072 mmol) as the starting material.

LRMS (APCI) calc'd for ($C_{19}H_{21}N_4O_4S$) $[M+H]^+$:401, Found: 401. JAK2 $IC_{50}$=20 nM.

Pharmaceutical Composition

As a specific embodiment of this invention, 100 mg of 3-{[4-(methylsulfonyl)phenyl]amino}-1-phenyl-1H-pyrazole-4-carboxamide is formulated with sufficient finely divided lactose to provide a total amount of 580 to 590 mg to fill a size 0, hard-gelatin capsule.

Biological Assays

JAK1 Enzyme Assay

For the JAK1 enzyme assay, reactions (50 uL) contained 5× IVGN buffer (50 mM Hepes, pH 7.5, 10 mM $MgCl_2$, 0.01% Brij-35, 1 mM EGTA, 0.1 mg/ml BSA), 2 mM DTT, 2.0 μM peptide substrate, 25 μM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDYFEWLE-NH2 (SEQ. ID NO.: 1); in DMSO.

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:
1. prepare 3-fold serial diluted compound/inhibitor solutions in 100% (DMSO) at 20× of the final desired concentrations in a 96 well plate;
2. prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-CONH$_2$) (SEQ. ID NO.: 1);
3. in a black assay plate, add 2.5 μl compound/inhibitor (or DMSO) and 37.5 μl master reaction mix per well; initiate the kinase reaction by adding 10 μl of 75 μM MgATP per well, allow the reactions to proceed for 80 minutes at room temperate; (the final conditions for the reactions are: 50 nM JAK2 JH1 domain (Upstate), 2.0 μM substrate, 15 μM MgATP, 5 mM $MgCl_2$, 100 mM NaCl, 2 mM DTT, 0.1 mg/ml BSA, 50 mM Tris (pH 7.4) and 5% DMSO);
4. stop the kinase reaction with 50 μl of Stop/Detection buffer containing 10 mM EDTA, 25 mM HEPES, 0.1% TRITON X-100, 0.126 μg/ml Eu-chelate labeled anti-phosphotyrosine antibody PY20 (cat. #AD0067, PerkinElmer) and 45 μg/ml Streptavidin-allophycocyanin conjugate (cat. # PJ25S, Prozyme); and
5. read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

Compounds of the instant invention are potent inhibitors of recombinant purified JAK2 kinase activity with an $IC_{50}$ of approximately 8 nM-1 μM.

JAK3 Enzyme Assay

For the JAK3 enzyme assay, reactions (50 uL) contained 5× IVGN buffer (50 mM Hepes, pH 7.5, 10 mM $MgCl_2$, 0.01% Brij-35, 1 mM EGTA, 0.1 mg/ml BSA), 2 mM DTT, 2.0 μM peptide substrate, 25 μM MgATP, 400 pM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDYFEWLE-NH2 (SEQ. ID NO.: 1); in DMSO.

TYK2 Enzyme Assay

For the TYK2 enzyme assay, reactions (50 uL) contained 5× IVGN buffer (50 mM Hepes, pH 7.5, 10 mM $MgCl_2$, 0.01% Brij-35, 1 mM EGTA, 0.1 mg/ml BSA), 2 mM DTT, 2.0 μM peptide substrate, 15 μM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDEPEGDYFEWLE-NH2 (SEQ. ID NO.: 1); in DMSO.

Assay For JAK Family Protein Kinase Activity

Materials: Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression: JAK3, TYK2 and JAK2 kinase domains with N-terminal "Flag" affinity tags were expressed in Sf9 cells using standard baculovirus methods. The human JAK3 gene and the human TYK2 gene can be purchased from Update (now part of Millpore Corporation). Human JAK2 kinase domain was cloned from a MOLT4 cDNA library (Clonetech).

Assay for JAK family protein kinase activity: Tyrosine kinase activity was measured by detection of the tyrosine phosphorylated peptide amino hexanoyl biotin-EQEDE-PEGDYFEWLE-NH2 (SEQ. ID NO.: 1); (S, hereafter) detected by time-resolved fluorescence using a europium labeled antibody to phosphotyrosine (pY20). The JAK3(JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM $MgCl_2$, 0.01% Brij-35, 1 mM EGTA, 0.1 mg/ml BSA), 2 mM (final) DTT, 2 µM (final) S, and 250 pM (final) JAK3 enzyme. The assay was run at ATP $K_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and $Em_1$=665 nm (SA-APC) and $Em_2$=615 nM (Eu). The data was analyzed by using a standard 4P fit on the ratio of the Em results: $(EM_1 \div EM_2)$ *10,000.

JAK2 384-Well HEL irfl-bla AlphaScreen™ SureFire™ p-STATS Assay:

Principle: When JAK2 is activated and dimerized, it phosphorylates STATS which translocates to the nucleus and actives the transcription of target genes. AlphaScreen™ SureFire™ p-STAT5 assay (Perkin Elmer and TGR Biosciences) uses both biotinylated anti-phospho-STAT5 antibody, which is captured by Streptavidin-coated Donor beads, and anti-total STAT5 antibody, which is captured by Protein A conjugated Acceptor beads. The irfl-b/a HEL CellSensor™ cell line was created by transducing parental HEL 92.1.7 cells (ATCC) with the pLenti-bsd/irfl-bla CellSensor™ vector. When both antibodies bind to phospho-STAT5 proteins released from HEL irfl-bla cells, the Donor and Acceptor beads are brought into the close proximity (<=200 nm) and a cascade of chemical reactions is initiated to produce a greatly amplified signal. Upon laser excitation, a photosensitizer in the donor bead converts ambient oxygen to a more excited singlet state. The singlet state oxygen molecules diffuse across to react with a chemiluminescer in the acceptor bead that further activates fluorophores contained within the same bead. The fluorophores subsequently emit light at 520-620 nm. The emitted light intensity is directly proportional to the amount of phospho-STAT5 proteins released from HEL irfl-bla cells.

Growth Medium: RPMI Medium 1640 (Invitrogen) with 10% dialyzed FBS (Invitrogen), 1 µg/ml blasticidin, 0.1 mM NEAA, 1 mM sodium pyruvate and 1% Pen-Strep.

Method: On day 1, split HEL irfl-bla cells at density of 500,000 cells/ml. Incubate cells in a tissue culture flask at 37° C., 5% $CO_2$ overnight. On day 2, harvest cells and wash the once with HBSS (Invitrogen) containing 0.5% dialyzed FBS. Next, seed cells at a density of 100,000 cells/well in 8 ul of HBSS w/0.5% dialyzed FBS in 384-well microliter plates. Temporarily put these cell plates in a 37° C., 5% $CO_2$ incubator. To prepare a compound plate, prepare serially diluted compounds in DMSO at a 500× stock concentration. Transfer 2 uL of the serially diluted compounds from the compound plate to an intermediate dilution plate containing 198 uL of HBSS w/ 0.5% dialyzed FBS. Next, transfer 2 uL of intermediately diluted compounds to each well of the cell plate to get 1:500 final dilution of each test compound and controls. Incubate the cell plates at 37° C., 5% $CO_2$ for 1 hr. Add 2.5 ul/well of 5× lysis buffer from the kit to cell plates. Gently agitate the plates for 5-10 min.

Make detection reagent mixture A by adding together 800 uL reaction buffer, 20 uL acceptor beads, and 200 uL activation buffer. Add 15 uL/well of detection mixture A to the cell plates and gently agitate the plates for 1-2 min. Seal the plates with an adhesive cover and incubate at room temperature for 2 hr, avoiding exposure to light. Make detection mixture B by adding together 400 uL dilution buffer and 20 uL donor beads. Add 6 uL/well of mixture B to the cell plates and gently agitate the plates for 1-2 min. Seal the plates with an adhesive cover and incubate at room temperature for 2 hr, avoiding exposure to light. Read the plates on an AlphaScreen-capable plate reader.

Cellular proliferation assays: CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5\times10^5$/ml. The next day, cells were washed and plated at $0.2-1\times10^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention are inhibitors of recombinant purified JAK3 kinase activity with an $IC_{50}$ of approximately >3000 nM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:

1. A compound of the following formula:

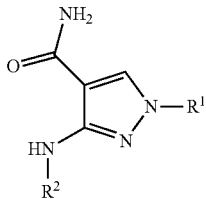

wherein $R^1$ is aryl, which is optionally substituted with one to three substituents independently selected from the group consisting of halo, hydroxyl, cyano, $SO_2R^3$, $C_{1-6}$ alkyl and heterocyclyl; wherein said alkyl group is optionally substituted with one to three halo, hydroxyl or cyano, and said heterocyclyl group is optionally substituted on either the carbon or heteroatom with one to three halo, hydroxyl or oxo;

$R^2$ is aryl or heteroaryl, wherein said aryl and heteroaryl groups are optionally substituted on either the carbon or heteroatom with one to three substituents selected from the group consisting of halo, cyano, $C_{1-6}$ alkyl, heterocyclyl, (C=O)heterocyclyl, (C=O)$R^3$, (C=O)$OR^3$, (C=O)$NR^3R^4$, $SO_2R^3$, $SO_2NR^3R^4$, $NR^3SO_2R^4$ and $SO_2$(heterocyclyl); wherein said alkyl group is optionally substituted with one to three halo, hydroxyl, O(C=O)$NR^3R^4$, heteroaryl, heterocyclyl or $NR^3R^4$; said heterocyclyl groups are optionally substituted on either the carbon or heteroatom with one to two groups independently selected from the group consisting of $C_{1-3}$ alkyl, hydroxyl and oxo; and said heteroaryl groups are optionally substituted on either the carbon or heteroatom with $C_{1-3}$ alkyl;

$R^3$ is hydrogen or $C_{1-6}$ alkyl;

$R^4$ is hydrogen or $C_{1-6}$ alkyl;

or a pharmaceutically acceptable salt thereof.

2. The compound of claim 1 wherein $R^1$ is aryl, wherein said aryl group is substituted with one to three substituents independently selected from the group consisting of halo and $C_{1-6}$ alkyl, wherein said alkyl group is optionally substituted with hydroxyl; or a pharmaceutically acceptable salt thereof.

3. The compound of claim 2 wherein $R^1$ is phenyl, wherein said phenyl group is substituted with one to three halo; or a pharmaceutically acceptable salt thereof.

4. The compound of claim 1 wherein $R^2$ is aryl or heteroaryl, wherein said aryl and heteroaryl groups are optionally substituted on either the carbon or heteroatom with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl, heterocyclyl or $NR^3R^4$; said heterocyclyl groups are optionally substituted on either the carbon or heteroatom with one to two groups independently selected from the group consisting of $C_{1-3}$ alkyl and oxo; or a pharmaceutically acceptable salt thereof.

5. The compound of claim 4 wherein $R^2$ is aryl, wherein said aryl group is optionally substituted with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl, heterocyclyl or $NR^3R^4$; said heterocyclyl groups are optionally substituted on either the carbon or heteroatom with one to two groups independently selected from the group consisting of $C_{1-3}$ alkyl and oxo; or a pharmaceutically acceptable salt thereof.

6. The compound of claim 5 wherein $R^2$ is phenyl, wherein said phenyl group is optionally substituted with one to three substituents selected from the group consisting of $C_{1-6}$ alkyl, (C=O)heterocyclyl, (C=O)$NR^3R^4$, $SO_2R^3$, $SO_2NR^3R^4$ and $SO_2$(heterocyclyl); wherein said alkyl group is optionally substituted with hydroxyl or heterocyclyl; said heterocyclyl groups are optionally substituted on either the carbon or heteroatom with one to two groups independently selected from the group consisting of $C_{1-3}$ alkyl, and oxo; or a pharmaceutically acceptable salt thereof.

7. The compound of claim 1 selected from

3-{[4-(methylsulfonyl)phenyl]amino}-1-phenyl-1H-pyrazole-4-carboxamide;

3-({4-[(methylamino)carbonyl]phenyl}amino)-1-phenyl-1H-pyrazole-4-carboxamide;

3-{[2-(hydroxymethyl)pyridin-4-yl]amino}-1-phenyl-1H-pyrazole-4-carboxamide;

3-{[4-(morpholin-4-ylcarbonyl)phenyl]amino}-1-phenyl-1H-pyrazole-4-carboxamide;

3-{[4-(morpholin-4-ylsulfonyl)phenyl]amino}-1-phenyl-1H-pyrazole-4-carboxamide;

3-({4-[(dimethylamino)sulfonyl]phenyl}amino)-1-phenyl-1H-pyrazole-4-carboxamide;

3-({4-[(dimethylamino)carbonyl]phenyl}amino)-1-phenyl-1H-pyrazole-4-carboxamide;

3-anilino-1-phenyl-1H-pyrazole-4-carboxamide;

3-({4-[(4-methylpiperazin-1-yl)carbonyl]phenyl}amino)-1-phenyl-1H-pyrazole-4-carboxamide;

3-({4-[(1,1-dioxidothiomorpholin-4-yl)carbonyl]phenyl}amino)-1-phenyl-1H-pyrazole-4-carboxamide;

3-{[4-(morpholin-4-ylmethyl)phenyl]amino}-1-phenyl-1H-pyrazole-4-carboxamide;

3-({4-[(1,1-dioxidothiomorpholin-4-yl)methyl]phenyl}amino)-1-phenyl-1H-pyrazole-4-carboxamide;

3-({4-[(dimethylamino)methyl]phenyl}amino)-1-phenyl-1H-pyrazole-4-carboxamide;

3-{[4-(1-hydroxy-1-methylethyl)phenyl]amino}-1-phenyl-1H-pyrazole-4-carboxamide;

1-(4-chlorophenyl)-3-{[4-(methylsulfonyl)phenyl]amino}-1H-pyrazole-4-carboxamide;

1-[4-(methylsulfonyl)phenyl]-3-{[4-(methylsulfonyl)phenyl]amino}-1H-pyrazole-4-carboxamide;

1-(4-tent-butylphenyl)-3-{[4-(methylsulfonyl)phenyl]amino}-1H-pyrazole-4-carboxamide;

1-[4-(1-hydroxyethyl)phenyl]-3-{[4-(methylsulfonyl)phenyl]amino}-1H-pyrazole-4-carboxamide;

or a pharmaceutically acceptable salt thereof.

8. A pharmaceutical composition comprising a pharmaceutically effective amount of the compound according to claim 1, and a pharmaceutically acceptable carrier.

\* \* \* \* \*

SEQUENCE LISTING

<160> NUMBER OF SEQ ID NOS: 1

<210> SEQ ID NO 1
<211> LENGTH: 15

```
<212> TYPE: PRT
<213> ORGANISM: Artificial Sequence
<220> FEATURE:
<223> OTHER INFORMATION: Completely synthetic amino acid
<220> FEATURE:
<221> NAME/KEY: AMIDATION
<222> LOCATION: (15)...(15)
<223> OTHER INFORMATION: Glutamic acid amide

<400> SEQUENCE: 1

Glu Gln Glu Asp Glu Pro Glu Gly Asp Tyr Phe Glu Trp Leu Glu
1               5                   10                  15
```